United States Patent [19]

Tureaud

[11] 4,175,322
[45] Nov. 27, 1979

[54] COMPLETE DENTURE PROSTHESES AND METHOD OF FITTING

[75] Inventor: Kenneth E. Tureaud, Ann Arbor, Mich.

[73] Assignee: Warner-Lambert Company, Morris Plains, N.J.

[21] Appl. No.: 835,143

[22] Filed: Sep. 21, 1977

[51] Int. Cl.² .............................................. A61C 13/00
[52] U.S. Cl. ..................................................... 433/171
[58] Field of Search ......................................... 32/2, 17

[56] References Cited

U.S. PATENT DOCUMENTS 3,727,309  4/1973  Huey .......................................... 32/2

FOREIGN PATENT DOCUMENTS 885595  8/1953  Fed. Rep. of Germany .............. 32/17

Primary Examiner—Robert Peshock
Attorney, Agent, or Firm—Albert H. Graddis; Frank S. Chow; David B. Ehrlinger

[57] ABSTRACT

A complete denture is disclosed for both maxillary and mandibular prostheses of the type having a hard base structure formed of acrylic plastic into which prosthetic teeth are set, the hard base structure fused to a deflectable tray layer of thermo plastic material which is deflectable when warm to adapt the denture to the general contours of the maxillary or mandibular ridges, a subsequent coating of autopolymerizing acrylic plastic being applied to the tray providing precise fitting of the denture to the oral contours of the wearer and stabilizing the soft deflectable tray in its newly achieved configuration. The hard base structure disclosed provides a tight bond to the prosthetic teeth and holds them securely in position in the occlusal plane but features a segmentation which allows lateral adjustment in the relative position of the posterior prosthetic teeth in each segment with respect to the teeth in the other segments to thus provide a capability for adjusting the prosthetic teeth to the maxillary or mandibular residual ridges. The segmentation in the preferred embodiment is provided by extending a thin juncture of deflectable material between two anterior teeth, i.e., the central incisors, to allow each half of the denture to be laterally shifted with respect to the other during fitting of the denture. Also disclosed, in the maxillary denture, is a pleat formed in that portion of the deflectable tray layer forming the palatal vault which serves to accommodate any shifting in position of the respective hard base structure segments. An alternate embodiment discloses the segmentation of the hard base structure into three segments, a first segment into which are mounted the anterior prosthetic teeth and two posterior teeth carrying segments. In the method of fitting the denture, the segments are laterally adjusted during fitting operation with respect to each other to align the prosthetic teeth with maxillary and mandibular ridges.

The resulting denture may be either directly used as a prosthesis or used as a model in constructing a final prosthesis.

20 Claims, 8 Drawing Figures

COMPLETE DENTURE PROSTHESES AND METHOD OF FITTING

BACKGROUND OF THE INVENTION

1. Field of the Invention

This invention concerns complete dentures and methods of fitting such dentures to wearers.

2. Description of the Prior Art

The major factor in the cost of prosthetic dentures at present is the difficulty involved in achieving a properly fitting denture, which fit is critical for comfort, proper mastication and appearance. Given the great variations in oral anatomy occurring among individuals and the critical nature of the fit, this fitting process has presented a very considerable technical challenge to dental science.

Very satisfactory materials for complete denture prostheses have been developed from a standpoint of durability, hardness, appearance, etc. These materials being those based on varying forms of acrylic plastics which are capable of providing the hardness and strength requirements and also of being colored to provide very aesthetically pleasing results.

However, the shaping of this material incidental to fitting of the denture to the patient's oral tissue contours by the direct molding of an acrylic plastic in its deflectable condition has heretofore been limited to reline procedures. This is due to the previous inability to confine and control the mass of material in an acceptable tray with prosthetic teeth fused to said tray, the configuration of which may be altered and shaped to fit the patient's oral anatomy. That is, in forming, some distortion of the tray would inevitably occur tending to misposition the prosthetic teeth relative each other. This would be particularly difficult in connection with the so-called "zero degree cuspal" teeth in which flat plane occlusion between the maxillary and mandibular dentures is produced, since any mislocation of the prosthetic teeth out of this plane would cause improper occlusion.

The use of deflectable acrylic as well as other alternative materials such as elastomeric materials for a tray having the prosthetic teeth molded are subject to a second even more serious drawback. Use of these materials has usually involved the bonding of the elastomeric materials to the prosthetic teeth which may be formed very satisfactorily from the aforementioned acrylic plastic or porcelain materials. However, the very considerable forces exerted on the denture during mastication by the wearer has had a tendency to open gaps between the deflectable acrylic or elastomeric material and the prosthetic teeth which allowed the entrance of food particles, with the subsequent relaxation of the forces trapping the good particles in the gaps, allowing bacterial growth and severe difficulties in maintaining the cleanliness of the dentures.

Adequate bonding of either the deflectable acrylic or elastomeric materials and the prosthetic teeth is impossible to achieve since the prosthetic materials generally do not bond to these materials in a highly satisfactory manner.

Accordingly, the conventional practice has involved complex and elaborate impression-taking procedures carried out over a period of several sessions, with a denture made to conform with the impression in order to properly fit the denture to the wearer's oral tissues. This fitting procedure accounts in large measure for the rather high expense of conventional dentures.

Attempts have been made to overcome these disadvantages, in which attempts a hard acrylic base structure is provided into which are fused the prosthetic teeth with the hard base structure receiving a deflectable thermo plastic tray bonded thereto which layer may be shaped at relatively low temperatures, compatible with human tissues to the general configuration of the patient's oral anatomy. As a final step, the molded deflectable plastic tray is lined with autompolymerizing acrylic plastic to produce a final shaping of the contour of the denture to the patient's oral cavity features. The partially set acrylic plastic is positioned within the patient's mouth, where final curing and fixating of the deflectable tray occurs.

This approach involves the use of an all-acrylic plastic structure insuring tight bonding between the deflectable tray layer and the hard base structure, but more importantly, firm anchoring of the prosthetic teeth to maintain their position during fitting and to prevent the entrance of bacteria and food particles between the prosthetic teeth and the hard base structure. Thus, this approach provides a practical but relatively quick-fitting procedure, while producing a denture having the necessary strength and stiffness requirement to preclude the deflection of the teeth and the opening of gaps in the denture into which food particles could otherwise become lodged. This denture is either used directly as a finished prosthesis or alternatively used as a model in the construction of a finished prosthesis.

This greatly reduces both the fitting and laboratory expense and thus the overall cost of obtaining the denture to the patient.

This concept utilizes, as an essential starting point, the U-shaped hard base structure in which the location of the prosthetic teeth are fixed. In the implementation of this concept, it is generally contemplated that a limited number of sizes of this hard base structure would be provided, with the molding steps of the deflectable tray accommodating the variations in maxillary or mandibular ridge configurations from that accorded by selection of sizes. While the various trays fit the majority of ridge variations, lateral positioning of the posterior teeth can be a critical factor in the ultimate success of the finished dentures. In addition, the aligning of the upper and lower teeth may not occur in severe skeletal patterns in which the lower jaw is much smaller than the upper jaw thus by the nature of size alone the teeth will not properly occlude.

Accordingly, it is an object of the present invention to provide a denture and a method of fitting such a prosthesis which allows the posterior prosthetic tooth lateral locations to be substantially altered to approximate the patient's residual gum ridge, obtaining the aforementioned advantages of a relatively simple fitting procedure in which the occlusal plane produces a hard and rigid unitary denture structure as a final result in which prosthetic teeth are securely retained so as to resist any deflecting forces, avoiding the opening of gaps such as may trap food particles.

It is another object of the present invention to produce a denture which may be provided to the patient at relatively low cost but will provide a well-fitting denture with good durability and function in terms of allowing the patient to masticate properly and which is aesthetically pleasing.

SUMMARY OF THE INVENTION

These and other objects, which will become apparent upon a reading of the following specification and claims, are accomplished by a denture in which a hard base structure is provided into which are set in proper location the prosthetic teeth, which hard base structure is segmented into at least two segments by virtue of a deflectable juncture section between segments of a deflectable material which allows the hard base structure segments to be laterally adjusted relative to each other during the fitting procedure to more nearly align the prosthetic teeth with either the mandibulary or maxillary residual ridges. The segmentation preferably is produced by a juncture or junctures between prosthetic teeth, corresponding to the frontal incisors.

In the preferred embodiment, the segmentation divides the denture into two segments by the juncture between the central incisors. In another version of the invention, the segmentation divides the denture into three segments by virtue of a pair of deflectable junctures producing an anterior tooth-bearing segment and two posterior tooth-bearing segments. The denture according to the present invention further includes the provision of a deflectable tray layer which is bonded molecularly to the base structure and adapted to be fit to the patient's mouth during the fitting operations and, in the case of a maxillary prosthesis, which deflectable tray layer may be formed with a pleat formed through median palatal suture portion of the deflectable tray. Any pleat void remaining after fitting would be filled with the acrylic plastic, utilized in the final fitting of the denture to the oral tissues of the wearer.

The denture so-produced may either be directly utilized as a prosthesis or alternatively used as a model for construction of a final prosthesis.

DETAILED DESCRIPTION

In the following detailed description, certain specific terminology will be utilized for the sake of clarity and specific embodiments described in accordance with 35 USC 112. However, it is to be understood that the invention is capable of taking many forms within the scope of the appended claims and the same is not intended to be limiting. For example, the invention will be described in terms of a maxillary denture but the concept is of course applicable to the mandibular denture as well. Similarly, the term "denture" as herein used is used to describe both dentures directly used as prostheses and those dentures used as models for construction of finished prostheses.

Figure 1:
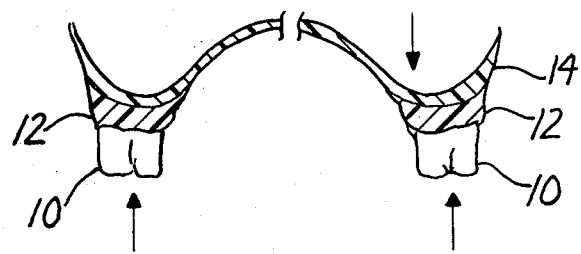
FIG. 1 is a sectional view through a maxillary denture according to the Prior Art in which the potential mispositioning of the prosthetic teeth with respect to the maxillary ridge is illustrated.
Figure 2:
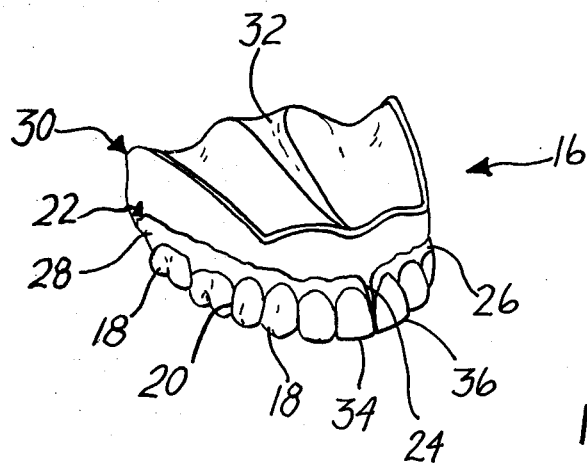
FIG. 2 is a perspective view of a maxillary denture according to the present invention in which the segmented hard base structure is incorporated.
Figure 3:
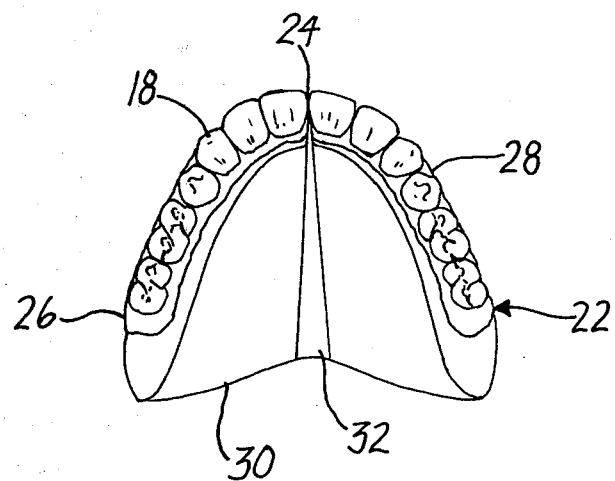
FIG. 3 is a plan view of the denture shown in FIG. 2.

Referring to the drawings, FIG. 1 demonstrates the situation which oftentimes occurs with the approach described in the description of the prior art. The denture includes a series of prosthetic teeth 10 which are cast into a hard base structure 12 so that the position with respect to each other and the posterior spacing of the prosthetic teeth is fixed by virtue of the base structure 12 and the prosthetic teeth 10 being formed into a unitary rigid structure. The deflectable tray 14 which is bonded to the hard base structure 12 is able to be formed and adapted within reasonable limits provided by the size selection, to conform the denture to the oral tissues as shown, but the prosthetic teeth 10 are somewhat offset with respect to the location of the wearer's maxillary ridge, as shown in the righthand side of the denture shown in FIG. 1. The arrows show the resulting offset between the point of application of the forces applied by the patient's upper jaw and the location of the prosthetic teeth 10, resulting in less effective masticatory function and also the shifting location of the teeth 10 with respect to the patient's mouth relative his natural dentition to therefore also possibly result in contour changes in the patient's face.

According to the concept of the present invention, the hard base structure and the prosthetic teeth 10 are not formed into a unitary rigid structure as per this prior art approach but rather the hard base structure is segmented, with a deflectable junction joining the segments to allow the position of the segments to be shifted laterally or adjusted relative to each other during fitting of the denture which creates a much more closely aligned location of the prosthetic teeth with respect to the residual ridges, or opposing dentition.

Thus, the aforementioned disadvantages may be largely avoided without resorting to a large number of standard modules of many differing sizes of the hard base structure 12.

Such a denture is illustrated in the drawings in FIGS. 2 through 5, the denture 16 including prosthetic teeth 18 which may be formed of a hard acrylic plastic as per conventional practice in which prosthetic teeth 18 are normally first joined together by means of an internal bar extending through the central portion of the teeth and the teeth additionally being cast so as to be bonded together along their proximal and lateral edges at 20 to provide a rigid assemblage of the prosthetic teeth. The hard base structure 22 is then cast or molded to the assemblage of teeth which material is also of a hard acrylic plastic, with the hard base structure 22 extending from the gum line of the denture a short distance above the teeth 18 to produce a tight assembly of the prosthetic teeth 18 to the hard base structure 22.

According to the present invention, the hard base structure 22 is not unitary or continuous, rather is segmented by the provision of a deflectable juncture 24 shown in this embodiment as extending between the central incisors 34 and 36 to produce segments 26 and 28 which are laterally adjustable with respect to each other to produce an adjustment in position of each posterior segment of the prosthetic teeth for the purposes described.

The juncture 24 may be provided by the filling in of a very thin layer of the deflectable material which forms the deflectable tray layer 30 which is normally provided in this type of denture construction. The deflectable tray is securely bonded to the hard base structure 22 and during molding of the assembly, a gap may be allowed to remain within the segments 26 and 28 which is filled with the deflectable material 30 of which the tray layer is formed. The central incisors 34 and 36 should thus be separately molded and not bonded along their mesial edges to accommodate this deflection incidental to adjustment of the denture.

The deflectable tray 30 is preferably formed with a pleat 32 which converges into the juncture area 24 and which acts to accommodate the relatively large movements of the prosthetic teeth 18 and the segments 26 and 28 with respect to each other.

Figure 5:
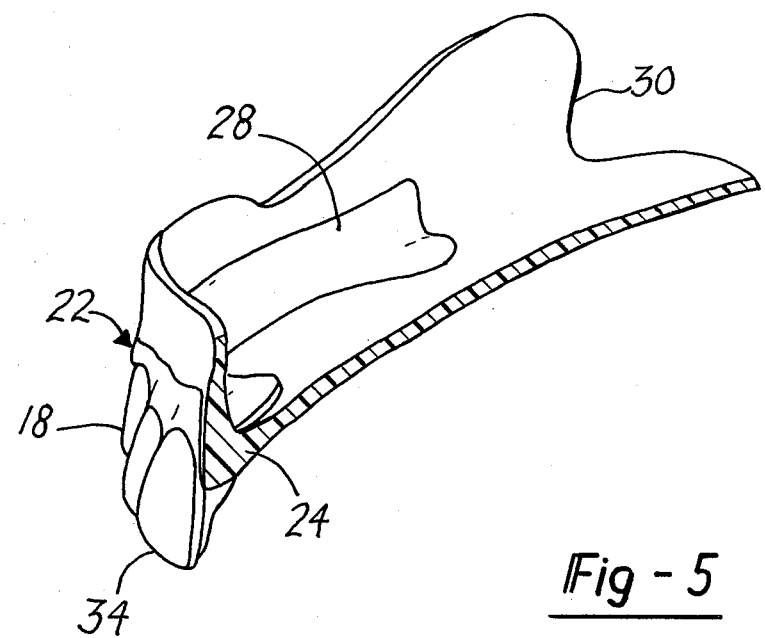
FIG. 5 is an enlarged perspective view of a section of the denture shown in FIGS. 2 through 4, further illustrating a method of creating the deflectable juncture formed between the hard base structure segments.
Figure 4:
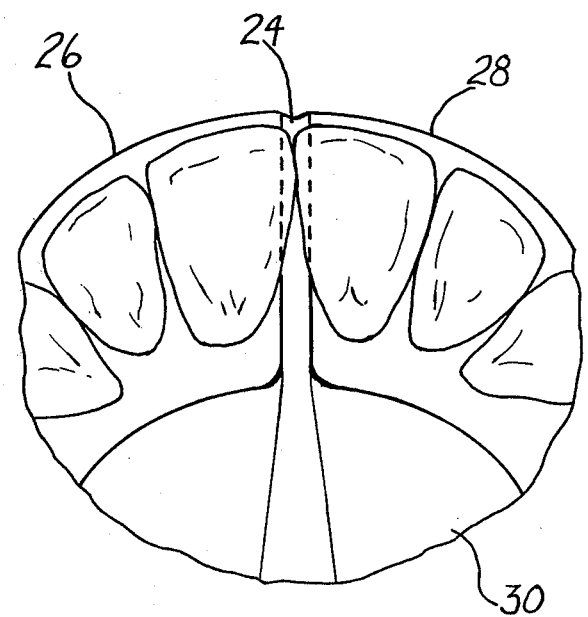
FIG. 4 is an enlarged sectional view of the denture shown in FIG. 3 showing the deflectable juncture formed between the segments of the hard base structure incorporated in FIG. 3.

The casting of the deflectable tray material is extended into the region of the juncture area 24, as shown in the enlarged view of FIG. 4, in which the deflectable material forming the tray 30 extends into the area between the segments 26 and 28 as best seen in FIG. 5.

The laterally deflectable relationship between the segments 26 and 28 thus is afforded by this construction.

Figure 6:
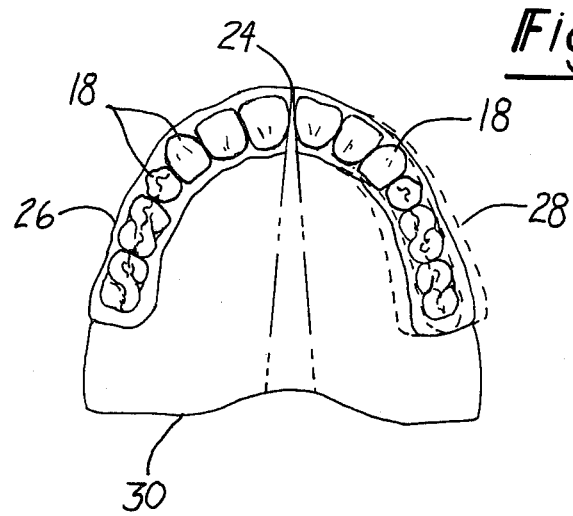
FIG. 6 is a plan view of the denture according to the present invention showing in phantom the adjustments of the segment of the hard base structure inwardly and outwardly to accommodate for different maxillary ridge locations.

In FIG. 6, the adjustment in position of the right segment 28 is indicated by the phantom lines showing an inward and an outward movement of the segment indicated. The juncture 24 is such as to maintain the position of the prosthetic teeth 18 in the occlusal plane defined by the teeth cusps while allowing the lateral adjustment described. Any minor distortions that may be introduced may be relatively easily corrected by the clinician after the molding step.

In the method of fitting the denture to the wearer, the denture would be initially placed in position in the patient's mouth with the denture 16 having been initially heated as by placing the same in warm water to render the deflectable material soft and the juncture 24 relatively pliable. The segments 28 and 26 would then be adjusted if necessary to align the maxillary posterior teeth with the residual ridge, the deflectable tray 30 then being molded into close proximity with the patient's mouth contours. The denture is then removed and hardened by freeze spraying or ice water chilling of the denture also per conventional practice.

The tissue side of the denture is then coated with autopolymerizing acrylic resin material with the various other conventional steps incidental to this step of course being carried out such as the coating of the areas subject to flash or overflow from the liner acrylic being coated with a petroleum material to prevent adhesions thereto of the flash. The denture would again be fitted within the patient's mouth with the final impression then being made and an initial hardening of the acrylic allowed to take place while the denture is in position in the patient's mouth. Since the polymerization reaction is generally exothermic, the complete curing of the denture generally takes place after removal from the patient's mouth and may be carried out with equipment familiar to those of ordinary skill in the art. Final fitting would involve the usual deburring, trimming, polishing and other operations well known to dental practitioners.

Alternatively, the final impression may be carried out by taking an impression of the patient's oral cavity, using the formed tray 30, making a model of the impression and forming the final detail of the tissue side of the tray 30 using the model.

Furthermore, the resulting denture may be used as a laboratory model in constructing a finished denture by encasing the denture in a mold, and removing the deflectable tray 30 and hard base structure 22, and casting in a hard base material in the configuration of the model, to produce a unitary, all-hard base material denture.

It should be noted that many steps and details involved in the alignment and fitting of these dentures have not been described herein since they do not form a part of the present invention and as they are well known to those clinicians skilled in this practice.

Figure 7:
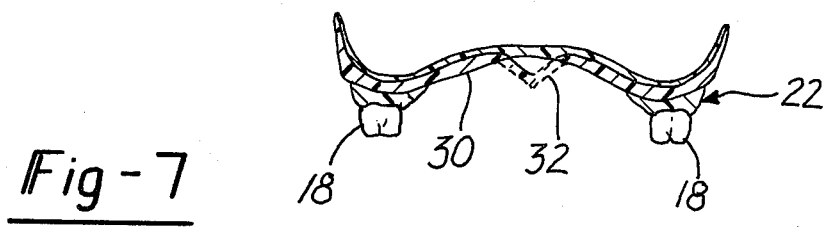
FIG. 7 shows a transverse sectional view in which the discontinuity created by the central pleat is removed during final finishing of the denture by filling of the crease void with the acrylic utilized during final curing of the prosthetic denture.

It can be seen by reference to FIG. 7, that the autopolymerizing acrylic resin will fill the void if any remaining created by the pleat 32 and the high point of the pleat 32 can be removed by deburring or grinding tools and the liquid material bridging the upper gap so that the liner layer 30 will again be of a smooth configuration.

It is further noted that the prosthetic teeth 18 will preferably be of the so-called "zero degree cuspal" configuration as described above in which the cusping shape of natural teeth is substantially eliminated so that the upper surface of the teeth while being sculpted, so as to give the appearance of being cusped, in fact bears level or zero degree grinding surfaces which makes proper fitting possible and reduces lateral stress on the residual ridges without aesthetic or comfort drawbacks. Using prosthetic teeth of this configuration in conjunction with the advantages afforded by the construction according to the present invention produces the end result of a complete denture which may be made at relatively low cost and may be fitted in a much shorter time to provide a high quality denture having satisfactory aesthetic, comfort and performance advantages at modest cost to the patient to enable a high quality denture to be afforded by virtually everyone.

Figure 8:
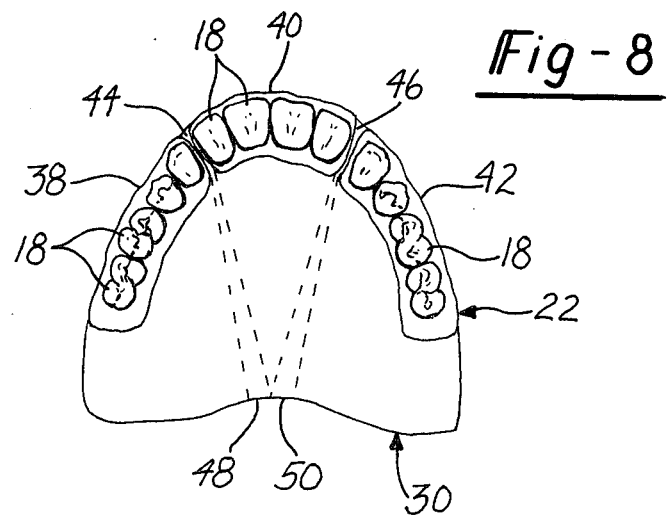
FIG. 8 shows an alternate version of the denture according to the present invention in which a plurality of segments are formed in the hard base structure.

While the segmentation disclosed in the above embodiment involves the juncture of one-half sections of the prosthetic teeth 18 defined by quadrants of natural dentition, another approach is shown in FIG. 8 in which a segmentation involves three segments extending between the cuspid and bicuspid teeth so that the posterior teeth in each quadrant may be laterally adjusted independently of the frontal incisors as shown so that the posterior spacing can be adjusted without effecting the position of the front incisors. Thus, three segments are formed, 38, 40 and 42, of the hard base structure 22 and two junctures 44 and 46 are provided which may be provided by similar methods as described above in conjunction with the first described embodiment. In this case, a pair of pleats 48 and 50 in the liner layer 30 may be provided. The junctures are similarly located in areas of minimal stress so that the juncture areas are similarly not as susceptible to strain and the small quantity of deflectable material utilized will not produce the above described disadvantages in connection with the deflection around the prosthetic teeth 18.

It can thus be seen that the prostheses according to the present invention obtain the advantages afforded by the above described prosthetic denture structure in which a hard base structure and soft deflectable layer bonded thereto is utilized without entailing the inherent disadvantages accruing from the use of a unitary rigid hard base structure since the hard base structure of the present invention offers lateral adjustment of the segments with respect to each other which is adequate to greatly improve the positioning of the prosthetic teeth to the residual maxillary or mandibular ridges. This has been achieved without any significant increase in the cost since only minor structural changes are necessitated but which, nonetheless, produce a very considerable advantage which substantially resolves the major drawbacks in the conventional directly formable prosthetic dentures.

Many variations of course are possible in the specifics disclosed since there are many approaches in the specifics of materials and the details of producing the exact fit such as the addition of a soft layer to the autopolymerized liner during the final forming step and variations in the configuration of the base structure for producing the deflectable juncture are of course necessary otherwise by molding the deflectable material of the soft liner layer 30.

It is also noted that many of the details of the manufacturing methods and materials have been omitted from the present application since these will be apparent to one of ordinary skill in the art and in themselves do not comprise the present invention.

The embodiments of the invention in which an exclusive property or privilege is claimed are defined as follows:

1. A denture comprising:
    a segmented hard base structure of a configuration generally in conformance with human mandibular or maxillary ridges, each segment of said hard base structure formed of a hard rigid material and means joining said segments together into said general configuration allowing said segments to be laterally adjusted in position relative to each other;
    a plurality of prosthetic teeth disposed about and bonded to the lower portion of each segment of said hard base structure, said prosthetic teeth shaped and positioned on said hard base structure so as to simulate human natural dentition;
    a deflectable tray layer bonded to said hard base structure, said deflectable tray layer being able to be molded to the wearer's oral contours during fitting thereof, whereby said segmented hard base structure may also be laterally adjusted during said fitting to align said prosthetic teeth generally with said mandibular or maxillary ridges.

2. The denture according to claim 1 wherein said means joining said segments comprises a region of said deflectable tray layer extending into a juncture between said segments.

3. The denture according to claim 1 wherein said deflectable tray layer includes a portion extending across said hard base structure to provide a palatal vault for the maxillary denture and wherein said portion is pleated so as to accommodate said adjustment movement of said segments of said hard base structure.

4. The denture according to claim 1 wherein each of said segments comprises one-half of said U-shaped hard base structure, joined between the prosthetic central incisors.

5. The denture according to claim 1 wherein said segments comprise at least three segments, joined between anterior and posterior sets of prosthetic teeth.

6. The denture according to claim 4 wherein said means joining said segments comprises a region of said deflectable layer extending into a juncture between said segments.

7. The denture according to claim 5 wherein said means joining said segments comprises a region of said deflectable layer extending into a juncture between said segments.

8. The denture according to claim 4 wherein said deflectable layer includes a portion extending across said hard base structure to provide a palatal vault for the maxillary denture and wherein said portion is pleated so as to accommodate said lateral adjustment movement of said segments of said hard base structure.

9. The denture according to claim 5 wherein said deflectable layer includes a portion extending across said hard base structure to provide a palatal vault for the maxillary denture and wherein said portion is pleated so as to accommodate said adjustment movement of said segments of said hard base structure.

10. The denture according to claim 1 wherein said prosthetic teeth are formed of hardened acrylic plastic and wherein said hard base structure is also formed of a hard acrylic plastic, said deflectable tray layer is formed from a thermo deflectable acrylic plastic.

11. The denture according to claim 6 wherein said prosthetic teeth are formed of hardened acrylic plastic and wherein said hard base structure is also formed of a hard acrylic plastic, said deflectable tray layer is formed from a thermo deflectable acrylic plastic.

12. The denture according to claim 7 wherein said prosthetic teeth are formed of hardened acrylic plastic and wherein said hard base structure is also formed of a hard acrylic plastic, said deflectable tray layer is formed from a thermo deflectable acrylic plastic.

13. The denture according to claim 8 wherein said prosthetic teeth are formed of hardened acrylic plastic and wherein said hard base structure is also formed of a hard acrylic plastic, said deflectable tray layer is formed from a thermo deflectable acrylic plastic.

14. The denture according to claim 9 wherein said prosthetic teeth are formed of hardened acrylic plastic and wherein said hard base structure is also formed of a hard acrylic plastic, said deflectable tray layer is formed from a thermo deflectable acrylic plastic.

15. The denture according to claim 1 wherein said prosthetic teeth are formed with substantially level cusps and are located in a flat occlusal plane by said hard base structure.

16. A method of adapting a prosthetic denture to human maxillary or mandibular oral contours, the method comprising:
    forming an assembly of prosthetic teeth shaped and located relative to one another to simulate the natural dentition, said assembly including a plurality of prosthetic teeth anchored in a generally U-shaped hard base structure generally conforming to the maxillary or mandibular ridges, said hard base structure being formed in segments joined with means enabling each segment to be adjustable in position with respect to each other and bonding a deflectable tray layer to said hard base structure;
    positioning said assembly in the mouth of the person to be fitted, with said deflectable tray layer positioned against the maxillary or mandibular ridge;

adjusting said segments with respect to each other to align said prosthetic teeth with said maxillary of mandibular residual ridge;

shaping said deflectable layer into the configuration of the oral tissues;

removing said assembly of prosthetic teeth from the person's mouth; and fixating said deflectable layer and said means joining said segments to produce a rigid unitary denture.

17. The method according to claim 16 further including the step of lining said deflectable tray with viscous material bondable to said deflectable tray after shaping said deflectable tray and repositioning said assembly in the person's mouth in selected position and hardening said viscous material after conforming said material to the contact oral tissues, whereby an exact fit is provided.

18. The method according to claim 17 wherein said hard base structure is formed from an acrylic plastic and said deflectable layer is formed from a thermo deflectable acrylic and said material is an autopolymerizing acrylic whereby setting of said acrylic produces fixation of said deflectable tray layer.

19. The method according to claim 17 wherein said segments are formed to comprise either half of said prosthetic teeth corresponding to a quadrant of natural dentition joined at the location of the prosthetic teeth corresponding to the central incisors.

20. The method according to claim 18 wherein said prosthetic teeth are formed from an acrylic plastic and bonded to said hard base structure.

* * * * *